(12) United States Patent
Cosatto et al.

(10) Patent No.: US 9,060,685 B2
(45) Date of Patent: Jun. 23, 2015

(54) WHOLE TISSUE CLASSIFIER FOR HISTOLOGY BIOPSY SLIDES

(71) Applicant: NEC Laboratories America, Inc., Princeton, NJ (US)

(72) Inventors: Eric Cosatto, Red Bank, NJ (US); Pierre-Francois Laquerre, North Brunswick, NJ (US); Christopher Malon, Fort Lee, NJ (US); Hans-Peter Graf, Lincroft, NJ (US)

(73) Assignee: NEC Laboratories America, Inc., Princeton, NJ (US)

( * ) Notice: Subject to any disclaimer, the term of this patent is extended or adjusted under 35 U.S.C. 154(b) by 147 days.

(21) Appl. No.: 13/850,694

(22) Filed: Mar. 26, 2013

(65) Prior Publication Data

US 2013/0315465 A1 Nov. 28, 2013

Related U.S. Application Data

(60) Provisional application No. 61/615,556, filed on Mar. 26, 2012, provisional application No. 61/740,623, filed on Dec. 21, 2012.

(51) Int. Cl.
| | |
|---|---|
| G06K 9/00 | (2006.01) |
| A61B 5/00 | (2006.01) |
| G06K 9/62 | (2006.01) |
| G06T 7/00 | (2006.01) |
| G06F 19/00 | (2011.01) |

(52) U.S. Cl.
CPC ............ *A61B 5/0033* (2013.01); *G06K 9/6227* (2013.01); *G06K 9/00127* (2013.01); *G06K 9/6256* (2013.01); *G06T 7/0012* (2013.01); *G06F 19/36* (2013.01); *G06T 2207/10056* (2013.01); *G06T 2207/20081* (2013.01); *G06T 2207/20084* (2013.01); *G06T 2207/30024* (2013.01)

(58) Field of Classification Search
None
See application file for complete search history.

(56) References Cited

U.S. PATENT DOCUMENTS

| | | | | |
|---|---|---|---|---|
| 6,819,790 | B2 * | 11/2004 | Suzuki et al. | 382/156 |
| 7,986,827 | B2 | 7/2011 | Rao | |
| 8,131,039 | B2 | 3/2012 | Krishnapuram | |
| 2008/0304733 | A1 * | 12/2008 | Macaulay et al. | 382/133 |

(Continued)

FOREIGN PATENT DOCUMENTS

EP 2434434 A3 2/2013

OTHER PUBLICATIONS

Babenko, Boris: "Multiple instance learning: algorithms and applications." View Article PubMed/NCBI Google Scholar (2008).*

(Continued)

*Primary Examiner* — Aaron W Carter
*Assistant Examiner* — Narek Zohrabyan
(74) *Attorney, Agent, or Firm* — Joseph Kolodka

(57) ABSTRACT

Disclosed is a computer implemented method for fully automated tissue diagnosis that trains a region of interest (ROI) classifier in a supervised manner, wherein labels are given only at a tissue level, the training using a multiple-instance learning variant of backpropagation, and trains a tissue classifier that uses the output of the ROI classifier. For a given tissue, the method finds ROIs, extracts feature vectors in each ROI, applies the ROI classifier to each feature vector thereby obtaining a set of probabilities, provides the probabilities to the tissue classifier and outputs a final diagnosis for the whole tissue.

8 Claims, 3 Drawing Sheets

(56) References Cited

U.S. PATENT DOCUMENTS

| | | | |
|---|---|---|---|
| 2010/0111396 A1* | 5/2010 | Boucheron | 382/133 |
| 2011/0255753 A1* | 10/2011 | Levenson et al. | 382/128 |
| 2012/0004514 A1 | 1/2012 | Marugame | |

OTHER PUBLICATIONS

Du, Xian, and Sumeet Dua. "Cancer prognosis using support vector regression in imaging modality." World journal of clinical oncology 2.1 (2011): p. 44-49.*

E. Cosatto et al., "Automated Gastric Cancer Diagnostics on H&E-stained sections; Large Scale Training with Multiple Instance Machine Learning", SPIE Medical Imaging: Digital Pathology (2013).

P-F Laquerre, "Multi-istance Active Feature Acquisition for Cancer Diagnosis", Apr. 5, 2011.

M. Ogura et al., "The e-Pathologist Cancer Diagnosis Assistance System for Gastric Biopsy Tissues", Analytical Cellular Pathology 34(4) 2011—pp. 177-178.

Z. Zhou et al., "Neural Networks for Multi-Instance Learning", Proceedings of the International Conference on Intelligent Information Technology, Beijing, China 2002.

T. Dietterich, "Solving the Multiple Instance Problem with Axis-Parallel Rectangles", Artificial Intelligence, 89(1-2):31-71, 1997.

M. Dundar et al., "A Multiple Instance Learning Approach Toward Optimal Classification of Pathology Slides", International Conference on Pattern Recognition, pp. 2732-2735, IEEE, 2010.

Y. Xu et al., "Multiple Clustered Instance Learning for Histophathology Cancer Image Classification, Segmentation and Clustering", International Conference on Pattern Recognition, 2012.

Y. Xu et al., "Contexts-Constrained Multiple Instane Learning for Histophathology Image Segmentation", Med Image Comput Assist Itner. 2012.

Z-H Zhou et al., "Multi-Instance Learning by Treating Instances as Non-I.I.D Samples", ICML 2009.

Chen et al., "MILES: Multiple-Instance Learning via Embedded Instance Selection" IEEE Transactions on Pattern Analytics and Machine Learning, vol. 28, No. 12 pp. 1931-1947, 2006.

D. Zhao et al., "Automated Classification of Human Histological Images, A Multiple-Instance Learning Approach", 2006 IEEE/NLM Life Science System and Applications Workshop.

J. Wang et al., "Solving the Multiple-Instance Problem: A Lazy Learning Approach", Proc. 17th International Conf. on Maching Learning.

C. Zhang et al., "A Multiple Instance Learning Approach for Content Based Image Retrieval Using One-Class Support Vector Machine" Proc. of IEEE International Conference on Multimedia & Expo (ICME) 2005.

* cited by examiner

WHOLE TISSUE CLASSIFIER FOR HISTOLOGY BIOPSY SLIDES

CROSS REFERENCE TO RELATED APPLICATIONS

This application claims the benefit of U.S. Provisional Patent Application Ser. No. 61/615,556 filed Mar. 26, 2012 and U.S. Provisional Patent Application Ser. No. 61/740,623 filed Dec. 21, 2012, for all purposes as if set forth at length herein.

TECHNICAL FIELD

This disclosure relates generally to the field of digital pathology and in particular to a computer implemented method providing for the fully automated diagnosis of an entire tissue on a histological slide.

BACKGROUND

One goal of digital pathology is to produce computerized systems that can detect the presence of cancer or other disease, possibly to be used as prescreening or quality control tools in coordination with human pathologists. To develop such systems, a machine learning classifier may be trained. Training data consists of examples of tissue, together with a grade indicating whether the tissue is cancerous or not. The grade typically describes the entire tissue without indicating the specific region where cancer may be found.

Digital images of biopsy specimens to be tested for the presence of disease, such as cancer, can be overwhelmingly large, possibly containing billions of pixels. While most of a tissue may appear healthy, disease-indicating phenomena may appear in a tiny fraction of the tissue to be examined.

The abundance of healthy tissue even in a tissue graded as cancerous poses a challenge for typical machine learning training methods. It may have the effect of lowering the quality of a trained classifier that randomly selects image regions inside cancerous and non-cancerous tissues and imputes the label of the tissue to them, because the random selections in cancerous tissue may look just like healthy tissue.

Multiple-instance learning is a class of machine learning techniques designed to address problems with non-specific labels. In the multiple-instance learning framework, a classifier considers so-called "bags" of examples, each of which consists of the same number of features. The features for all the examples together are used to classify the bag.

In digital pathology, a multiple-instance learning setting may be constructed by dividing a tissue into so-called "regions of interest" (ROI), each of which is used to measure a set of features. The ROI may be selected heuristically and may not cover the entire tissue. The multiple-instance learning task is to classify the entire tissue using the features from the set of ROI.

This invention separates the training of a tissue classifier into two parts. The first part is the training of an ROI classifier with the objective of minimizing the error given by the maximum decision over all ROI in the tissue. The second part is the training of a tissue classifier based on actual ROI outputs. Compared to non-multiple-instance learning approaches, the first part confers the advantage of not assuming that all the tissue in a cancerous tissue is actually cancerous. Compared to using the multiple instance classifier obtained through the first part alone, introducing the second part may improve the tissue classification result by learning to aggregate noisy ROI decisions in the best way.

SUMMARY

This invention separates the training of a histological tissue classifier into two parts. The first part is the training of a multiple instance ROI classifier with the objective of minimizing the error given by the maximum decision over all ROI in the tissue. The second part is the training of a tissue classifier based on actual ROI outputs. Compared to non-multiple-instance learning approaches, the first part confers the advantage of not assuming that all the tissue in a cancerous tissue is actually cancerous. Compared to using the multiple instance classifier obtained through the first part alone, introducing the second part may improve the tissue classification result by learning to aggregate noisy ROI decisions in the best way.

BRIEF DESCRIPTION OF THE DRAWING

A more complete understanding of the present disclosure may be realized by reference to the accompanying drawing in which.

DETAILED DESCRIPTION

Figure 1:
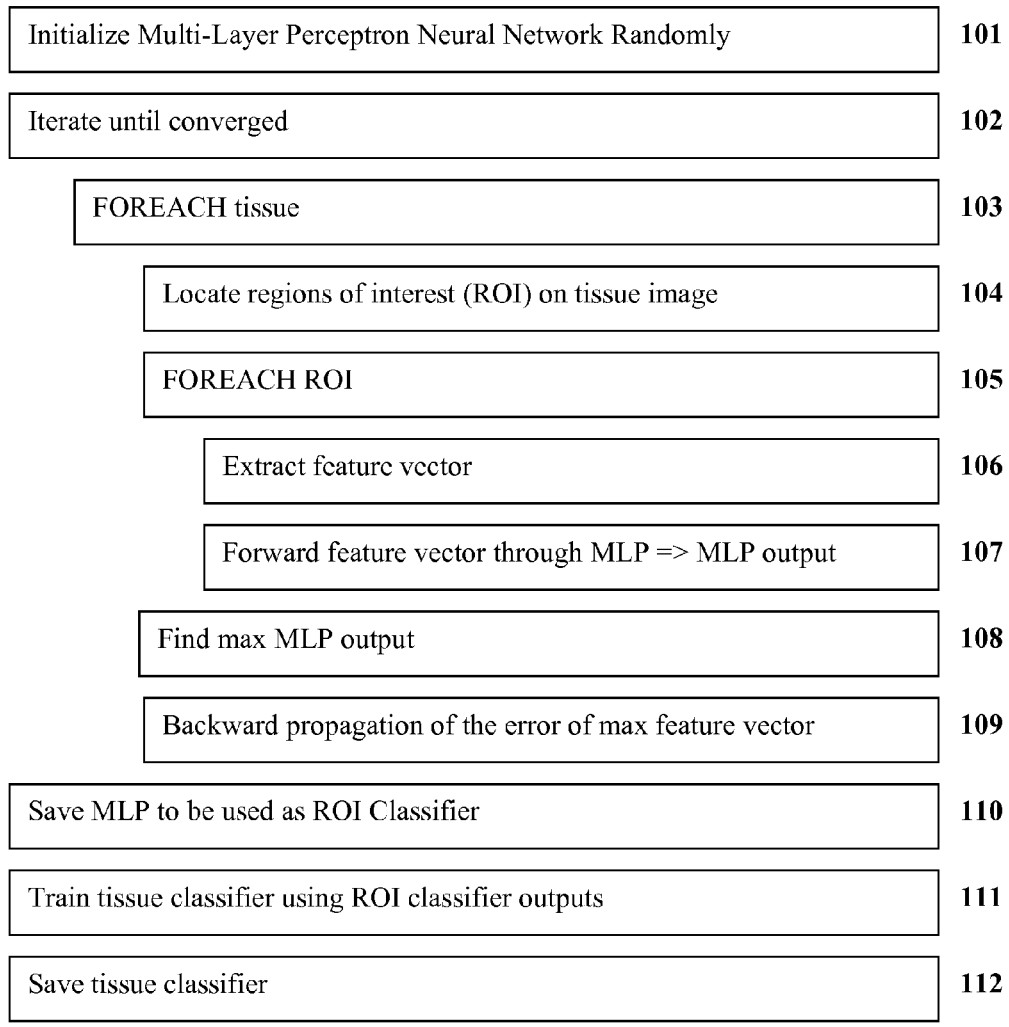
FIG. 1 is a flow diagram depicting the training phase according to aspects of the present disclosure.

The following merely illustrates the principles of the disclosure. It will thus be appreciated that those skilled in the art will be able to devise various arrangements which, although not explicitly described or shown herein, embody the principles of the disclosure and are included within its spirit and scope.

Furthermore, all examples and conditional language recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions.

Moreover, all statements herein reciting principles, aspects, and embodiments of the disclosure, as well as specific examples thereof, are intended to encompass both structural and functional equivalents thereof. Additionally, it is intended that such equivalents include both currently-known equivalents as well as equivalents developed in the future, i.e., any elements developed that perform the same function, regardless of structure.

Thus, for example, it will be appreciated by those skilled in the art that the diagrams herein represent conceptual views of illustrative structures embodying the principles of the invention.

In addition, it will be appreciated by those skilled in art that any flow charts, flow diagrams, state transition diagrams, pseudo code, and the like represent various processes which may be substantially represented in computer readable medium and so executed by a computer or processor, whether or not such computer or processor is explicitly shown.

In the claims hereof any element expressed as a means for performing a specified function is intended to encompass any way of performing that function including, for example, a) a combination of circuit elements which performs that function or b) software in any form, including, therefore, firmware, microcode or the like, combined with appropriate circuitry for executing that software to perform the function. The invention as defined by such claims resides in the fact that the functionalities provided by the various recited means are combined and brought together in the manner which the claims call for. Applicant thus regards any means which can provide those functionalities as equivalent as those shown herein. Finally, and unless otherwise explicitly specified herein, the drawings are not drawn to scale.

Thus, for example, it will be appreciated by those skilled in the art that the diagrams herein represent conceptual views of illustrative structures embodying the principles of the disclosure.

By way of some additional background, we begin by noting that training an instance classifier with bag-level labels (where a bag contains multiple instance(s)), has been pursued and described in machine learning literature and is generally known as multi-instance learning. Methods have been described, (See, e.g., T. Dietterich, "Solving The Multiple Instance Problem with Axis-Parallel Rectangles", Artificial Intelligence, 89, (1-2): 31-71, 1997; Z. H. Zhou, Y. Y. Sun, and Y. F. Li, "Multi-Instance Learning by Treating Instances and Non-I.I.D. Samples", Proceedings of the 26$^{th}$ Annual International Conference on Machine Learning—ICML '09, pp. 1-8; J. Wang and J. D. Zucker, "Solving the Multiple-Instance Problem: A Lazy Learning Approach", 17$^{th}$ International Conference on Machine Learning, pp. 1119-1125, 2000), but such methods have never been applied to digital pathology. While methods such as those disclosed methods do advance the art, they are limited by the fact that they do not learn a new bag-level classifier on top of the instance classifier, or simply do not produce an intermediate instance classifier at all.

As will become apparent to those skilled in the art, the present disclosure is directed to the training of a histological, whole-tissue classifier while advantageously increasing its accuracy. Furthermore, methods according to the present disclosure eliminate the need for fine-grain labeling of tissues. Still further, methods according to the present disclosure take advantage of a large amount of existing labeled tissue to train the classifier with many examples, thereby making the classifier and resulting classifications more robust. Additionally, a further advantage—and depending upon the type of tissue-level classifier—methods according to the present disclosure may be made faster by stopping as soon as one of the regions of interests is diagnosed, for example, is cancerous. Lastly, training methods according to the present disclosure may be advantageously applied to any error function compatible with standard backpropagation.

In sharp contrast, fine-grain labeling is a major obstacle in traditional approaches due to the fact that trained pathologists have to be employed at significant cost. Additionally, tools required to efficiently label tissue images are costly to develop, setup, and maintain.

As previously noted, methods according to aspects of the present disclosure first segment relevant parts of tissue image (s) in to a set of processing units we call regions of interest (ROI). Each ROI is then processed to extract a vector of numerical features. Using a multi-instance learning approach, we train a Multi-Layer Perceptron (MLP) using back propagation wherein only the error of the maximal response among the units of tissue is back-propagated while updating the parameters of the MLP in a manner that reduces the output error. Finally, a tissue classifier is trained such that it takes the outputs of the ROI classifier and produces a classification for the entire tissue.

Turning now to FIG. 1, there is shown a flow diagram showing a training procedure according to an aspect of the present disclosure. More particularly, the flow diagram depicts the computer implemented steps of a training procedure for a whole-tissue classifier. Generally, it involves the training of a multi-layer perceptron neural network to classify ROI entities as cancerous or normal (i.e., the output value is the probability of the ROI being cancerous).

At step 101, the multi-layer Perceptron neural network is initialized randomly. After initialization, an interactive process (step 102) "loops" over all tissues (step 103) wherein regions of interest are located and extracted (step 104) by a chosen method.

At this point it is notable that an ROI may take any shape or may be the result of an automatic segmentation of the image.

The process then continues and loops over all ROIs (step 105). For a given ROI, features are extracted from its image (step 106) and "fed" through the MLP, resulting in an MLP output value (step 107). Notably, no particular feature extraction process, nor extracted features are specified here; advantageously they may be any useful feature that helps facilitate the ROI (as cancerous or normal—for example).

The input feature vector that generates the largest (max) output value (step 108) within all ROIs of a tissue is considered for back propagation of the error (step 109). The error function used herein is the negative log-likelihood NLL, which is represented by the following relationship:

$$NLL = t(\ln(\text{out})) - (1-t)(\ln(1-\text{out}))$$

wherein t is the tissue label (0 if normal, 1 if cancerous) and out is the MLPs output probability. As may be appreciated, this procedure has the effect of de-emphasizing the ROI with the highest output value when the tissue is negative and emphasizing it when the tissue is positive. Advantageously, this method may be applied to any error function typically used to train MLPs.

Finally, the process loops back and revisits all tissues in the training set until convergence is reached as defined by a stopping criterion (step 102).

At this point, the ROI classifier is fixed and saved to be used in the training of a tissue classifier (step 111) that takes as input the ROI classifier outputs. As those skilled in the art will appreciate, there are a number of ways to achieve the classification—the simplest being to declare the tissue cancerous if one ROI has a high probability of being cancerous (above a certain threshold). In this case the training phase only picks a threshold using the training set ROC (receiver operating characteristic) curve. Advantageously, the approach may be extended by tuning multiple thresholds, resulting in a rule-based classifier. For example, a tissue is declared cancerous if p % of ROIs are over a threshold t. Another approach is to build a histogram of probabilities and use it as input to a standard classifier such as a Support Vector Machine (SVM). Once trained, both the ROI (step 110) and the tissue (step 112) are saved for use by the online phase.

Figure 2:
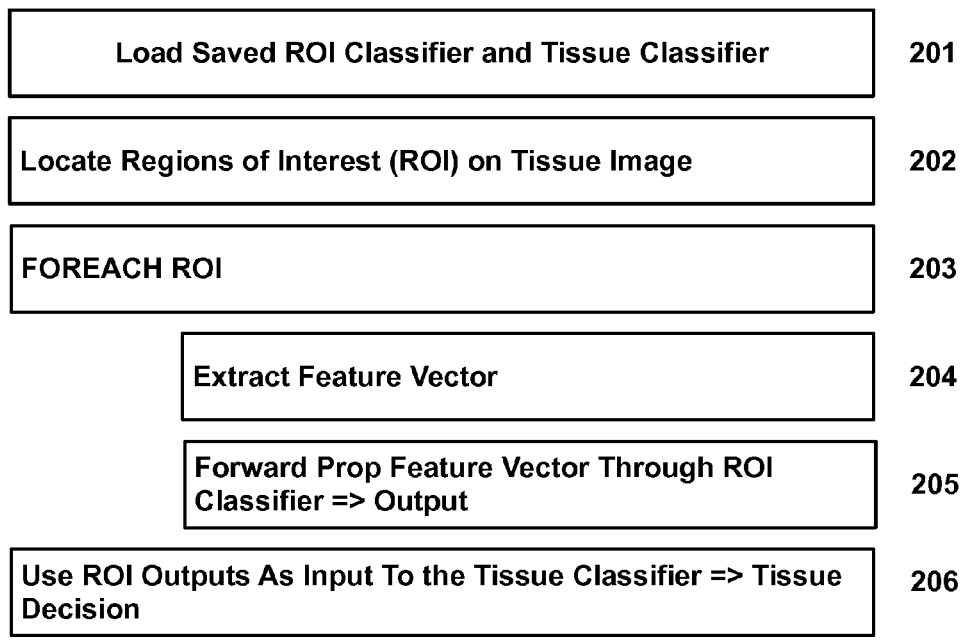
FIG. 2 is a flow diagram that depicts the on-line phase determination according to an aspect of the present disclosure.

With reference now to FIG. 2 there is shown a flow diagram depicting the steps associated with the online phase. More particularly, during this online phase, the saved ROI classifier and tissue classifier that are obtained during the training phase are loaded (step 201). On the given tissue image, regions of interest (ROIs) are located on the tissue image (step 202). For each ROI (step 203), a feature vector is extracted (step 204), and the feature vector so extracted is forward propagated through ROI classifier (step 205) giving the probability—for this example—of the tissue being cancerous. The probabilities of all ROIs (ROI outputs) are then combined and used as inputs to the tissue classifier which leads to an overall tissue decision (step 206).

Figure 3:
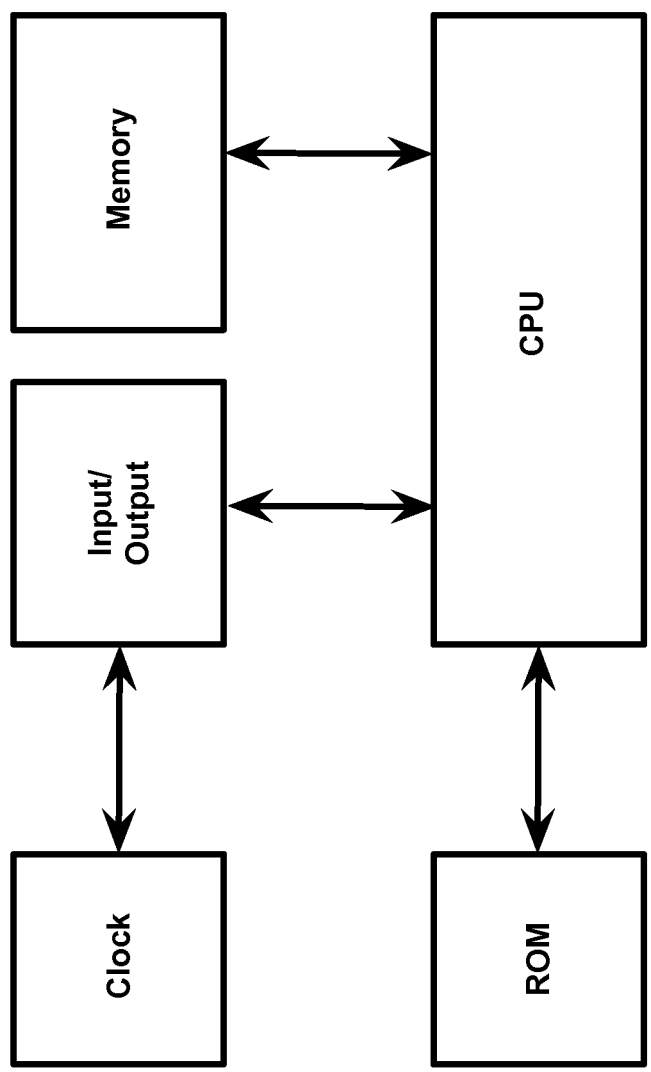
FIG. 3 is a block diagram depicting a representative computer system according to an aspect of the present disclosure.

FIG. 3 shows a schematic block diagram of a representative computer system in/upon which methods and systems according to the present disclosure may be constructed.

At this point, the foregoing is to be understood as being in every respect illustrative and exemplary, but not restrictive, and the scope of the invention disclosed herein is not to be determined from the Detailed Description and APPENDIX A, but rather from the claims as interpreted according to the full breadth permitted by the patent laws. It is to be understood that the embodiments shown and described herein (including APPENDIX A) are only illustrative of the principles of the present invention and that those skilled in the art may implement various modifications without departing from the scope and spirit of the invention. Those skilled in the art could implement various other feature combinations without departing from the scope and spirit of the invention.

The invention claimed is:

1. A computer-implemented method of whole tissue classification steps of:
   training a Multi-Layer Perceptron (MLP) classifier in a supervised manner wherein labels are given only at a tissue level, the training using a multiple-instance learning variant of backpropagation, wherein an input feature vector that generates the largest output value within all regions of interest (ROI) is back-propagated;
   training a tissue classifier with an output of the MLP classifier;
   for a given tissue image:
      segmenting the tissue image into ROIs;
      extracting a vector of features from each of the ROIs;
      applying the MLP classifier to the vector of features of each ROI thereby obtaining a set of probabilities;
      providing the probabilities to a tissue classifier; and
      outputting a diagnosis of the whole-tissue.

2. The method of claim 1 wherein tissue classifier comprises a support vector machine (SVM) which receives as input a histogram of individual ROI probabilities.

3. The method of claim 1 wherein the tissue classifier comprises a support vector regression (SVR) which receives as input a histogram of the ROI probabilities and outputs a tissue histological grade.

4. The method of claim 1, wherein the probabilities obtained from the MLP classifier are provided to a downstream system.

5. A system for performing whole-tissue classification, said system comprising a computing device including a processor and a memory coupled to said processor, said memory having stored thereon computer executable instructions that upon execution by the processor cause the system to:
   train a Multi-Layer Perception (MLP) classifier in a supervised manner wherein labels are given only at a tissue level, the training using a multiple-instance learning variant of backpropagation, wherein an input feature vector that generates the largest output value within all regions of interest (ROI) is back-propagated;
   train a tissue classifier with an output of the MLP classifier;
   for a given tissue image:
      segment the tissue image into ROIs
      extract a vector of features from each of the ROIs;
      apply the MLP classifier to the vector of features of each ROI thereby obtaining a set of probabilities;
      provide the probabilities to a tissue classifier; and
      output a diagnosis of the whole-tissue.

6. The system of claim 5 wherein tissue classifier comprises a support vector machine (SVM) which receives as input a histogram of individual ROI probabilities.

7. The system of claim 5 wherein the tissue classifier comprises a support vector regression (SVR) which receives as input a histogram of the ROI probabilities and outputs a tissue histological grade.

8. The system of claim 5, wherein the probabilities obtained from the MLP classifier are provided to a downstream system.

\* \* \* \* \*